US006969360B1

(12) United States Patent
Pai et al.

(10) Patent No.: US 6,969,360 B1
(45) Date of Patent: Nov. 29, 2005

(54) SPINAL PROPRIOCEPTION METHODS AND RELATED SYSTEMS

(75) Inventors: Clive Pai, North Riverside, IL (US); Cheryl Petersen, Port Washington, WI (US); Arvid Brekke, Esko, MN (US); Mary Ellen Bulow, Palos Heights, IL (US); Erinn Ewers, Chicago, IL (US)

(73) Assignee: Northwestern University, Evanston, IL (US)

( * ) Notice: Subject to any disclaimer, the term of this patent is extended or adjusted under 35 U.S.C. 154(b) by 314 days.

(21) Appl. No.: 10/075,120

(22) Filed: Feb. 13, 2002

Related U.S. Application Data (60) Provisional application No. 60/268,296, filed on Feb. 13, 2001.

(51) Int. Cl.[7] ............................................. A61B 5/103
(52) U.S. Cl. ...................... 600/594; 600/587; 600/595
(58) Field of Search ............................... 600/587, 594, 600/595; 33/511, 512; 601/23, 24, 90, 91, 601/98; 482/140, 148

(56) References Cited

U.S. PATENT DOCUMENTS

| | | | | |
|---|---|---|---|---|
| 5,101,835 | A * | 4/1992 | DelRe ......................... | 600/594 |
| 5,188,121 | A * | 2/1993 | Hanson ....................... | 600/594 |
| 5,192,305 | A * | 3/1993 | Sastre ......................... | 606/241 |
| 5,443,079 | A * | 8/1995 | Greenawalt ................. | 600/594 |
| 5,758,658 | A * | 6/1998 | Petragallo ................... | 600/595 |
| 5,776,082 | A * | 7/1998 | Riley et al. ................. | 600/594 |
| 6,325,767 | B1 * | 12/2001 | Wolff et al. ................. | 600/587 |
| 6,692,449 | B1 * | 2/2004 | Brown ......................... | 600/595 |

FOREIGN PATENT DOCUMENTS

| | | | | |
|---|---|---|---|---|
| FR | 2664152 | A * | 1/1992 | ............ A61B 5/11 |

OTHER PUBLICATIONS

Roy, et al., Fatigue, recovery, and low back pain in varsity rowers, Medicine and Science in Sports and Exercise, vol. 22, No. 4, 1989, pp. 463-469.

Roy, et al., Lumbar Muscle Fatigue and Chronic Lower Back Pain, SPINE, vol. 14, No. 9, 1989, pp. 992-1000.

O'Sullivan, et al., Evaluation of Specific Stabilizing Exercise in the Treatment of Chronic Low Back Pain With Radiologic Diagnosis of Spondylolysis or Spondylolisthesis, SPINE, vol. 22, No. 24, 1997, pp. 2959-2967.

Fritz, et al., Segmental Instability of the Lumber Spine, Physical Therapy, vol. 78, No. 8, Aug. 1998, pp. 889-894.

Taimela, et al., The Effect of Lumbar Fatigue on the Ability to Sense a Change in Lumbar Position, SPINE, vol. 24, No. 13, 1999, pp. 1322-1327.

Gill, et al., The Measurement of Lumbar Proprioception in Individuals With and Without Low Back Pain, SPINE, vol. 23, No. 3, 1998, pp. 371-377.

Koumantakis, et al., Toracolumbar Proprioception in Individuals With and Without Low Back Pain: Intratester Reliability, Clinical Applicability, and Validity, Journal of Orthopaedic & Sports Physical Therapy, vol. 32, No. 7, Jul. 2002, pp. 327-335.

Brumagne, et al., Effect of Paraspinal Muscle Vibration on Position Sense of the Lumbosacral Spine, SPINE, vol. 24, No. 13, pp. 1328-1331, 1999.

(Continued)

Primary Examiner—Charles Marmor
(74) Attorney, Agent, or Firm—Reinhart Boerner Van Deuren s.c.

(57) ABSTRACT

A system, device and/or method for measuring spinal proprioception, as can be used to screen proprioceptive loss and/or improvement after treatment.

18 Claims, 6 Drawing Sheets

OTHER PUBLICATIONS

Brumagne, et al., Lumbosacral Position Sense During Pelvic Tilting in Men and Women Without Low Back Pain: Test Development and Reliability Assessment, Journal of Orthopaedic & Sports Physical Therapy, vol. 29, No. 6, 1999, pp. 345-351.

Lam, et al., Lumbar Spine Kinestesia in Patients with Low Back Pain, Journal of Orthopaedic & Sports Physical Thearpy, vol. 29, No. 5, 1999, pp. 294-299.

Parkhurst, et al., Injury and Proprioception in the Lower Back, Journal of Orthopaedic & Sports Physical Therapy, vol. 19, No. 5, 1994, pp. 282-295.

Swinkels; et al., Regional Assessment of Joint Position Sense in the Spine, SPINE, vol. 23, No. 5, 1998, pp. 590-597.

Swinkels, et al., Spinal Position Sense Is Independent of the Magnitude of Movement, SPINE, vol. 25, No. 1, 2000, pp. 98-105.

Maffey-Ward, et al., Toward a Clinical Test of Lumbar Spine Kinesthesia, Journal of Orthopaedic & Sports Physical Therapy, vol. 24, No. 6, Dec. 1996, pp. 354-358.

Newcomer, et al., Repositioning Error in Low Back Pain, SPINE, vol. 25, No. 2, 2000, pp. 245-250.

Roy, et al., Fatigue, recovery, and low back pain in varsity rowers, Medicine and Science in Sports and Exercise, vol. 22, No. 4, 1990, pp. 463-469.

Fritz, et al., Segmental Instability of the Lumbar Spine, Physical Therapy, vol. 78, No. 8, Aug. 1998, pp. 889-894.

Amonoo-Kuofi, The number and distribution of muscle spindles in human intrinsic postvertebral muscles. J. Anat. 1982; 135-585-99.

Ashton-Miller, et al., Trunk positioning accuracy in children 7-18 years old. J Orthop Res. 1992; 10:217-25.

Barrack, et al., Proprioception in the anterior cruciate deficient knee. The American Journal of Sports Medicine. 1989; 17(1):1-6.

Barrett, et al., Joint proprioception in normal, osteoarthritic and replaced knees. J Bone Joint Surg [BR]. 1991; 73:53-6.

Barrett. Proprioception and function after anterior cruciate reconstruction. J Bone Joint Surg. Br. 1991; 73:833-837.

Corrigan, et al., Proprioception in the cruciate deficient knee. J Bone Joint Surgery. 1992; 74B:247-250.

Esola, et al., Analysis of lumbar spine and hip motion during forward bending in subjects with and without a history of low back pain. Spine. 1996; 21(1):71-78.

Fairbanks, et al. The oswestry low back disability pain questionaire. Physiotherapy. 1980; 6:271-273.

Farfan, Muscular mechanism of the lumbar spine and the position of power and efficiency. Orthopedic Clinincs of North America. 1975; 6(1):135-144.

Fritz, et al. Improving neuromuscular control following trunk and lumbar spine injury. The professional journal for athletic trainers and therapists. 1998; 19-28.

Freeman, et al. The etiology and prevention of functional instability of the foot. J Bone Joint Surg. 1965; 47B:678-685.

Gandevia, et al. Does the nervous system depend on kinesthetic information to control natural limb movements? Behavioral and Brain Sciences. 1992; 15(4):614-632.

Gandevia, et al. Proprioceptive sensation at the terminal joint of the middle finger. J Physiol. 1983; 335:507-517.

Gandevia, et al. Joint sense, muscle sense and their combination as position sense, measured at the distal interphalangeal joint of the middle finger. J Phsiol. 1976; 260:387-407.

Glencross, et al. Position sense following joint injury. J Sports Med. 1981; 21:23-27.

Goodwin, et al. The persistence of appreciable kinesthesis after paralyzing joint afferents but preserving muscle afferents. Brain Research. 1972; 37:326-329.

Grigg. Peripheral neural mechanisms in proprioception. J Sport Rehabil. 1994; 3:2-17.

Hagins, et al. Effects of practice on the ability to perform lumbar stabilization exercises. JOSPT. 1999; 29(9):546-555.

Hides, et al. Multifidus muscle recovery is not automatic after resolution of acute, first-episode low back pain. Spine. 1996; 21(23):2763-2769.

Hides, et al. Evidence of lumbar multifidus muscle wasting ipsilateral to symptoms in patients with acute/subacute low back pain. Spine. 1994; 19(2):165-172.

Jakobs, et al. Trunk position sense in the frontal plane. Exp Neurol. 1985; 90:129-38.

Johannsen, et al. Exwecises for chronic low back pain: a clinical trial. JOSPT. 1995; 22(2):52-59.

Kaplan, et al. Age-related changes in proprioception and sensation of joint position. Acta Orthop Scand. 1985; 56: 72-74.

Loudon, et al. Ability to reproduce head position after whiplash injury. Spine. 1997; 22(8):865-868.

Marks, et al. Proprioceptive sensibility in women with normal and osteoarthritic knee joints. Clinical Rheumatology. 1993; 12(2):170-175.

Martin, et al. Anatomy of the somatic sensory system. In: Kandel, et al., eds. Principles of Neural Science. Norwalk: Appleton & Lange; 1991:353-366.

Matthews. Proprioceptors and their contribution to somatosensory mapping: complex messages require complex processing. Can J Physiol Pharmacol. 1988; 66: 430-438.

McClure, et al. Kinematic analysis of lumbar and hip motion while rising from a forward, flexed position in patients with and without a history of low back pain. Spine. 1997; 22(5):552-558.

McLain, et al. Mechanoreceptor endings of the cervical, thoracic, and lumbar spine, Iowa Orthopedic Journal. 1995; 15:147-155.

McLain. Mechanoreceptor endings in human cervical facet joints, Spine. 1994; 19:495-501.

McNair, et al. Trunk proprioception enhancement through lumbar bracing. Archives of Phys Medicine and Rehabilitation. 1999; 80;96-99.

Nelson, et al. Relative lumbar and pelvic motion during loaded spinal flexion/extension. Spine. 1995; 20(2):199-204.

Paquet, et al. Hip-spine movement interaction and muscle activation patterns during sagittal trunk movements in low back pain patients. Spine. 1994; 19(5):596-603.

Revel, et al. Cervicocephalic kinesthetic sensibility in patients with cervical pain. Arch Phys Med Rehabil. 1991; 72:288-291.

Revel, et al. Changes in cervicocephalic kinesthesia after a proprioceptive rehabilitation program in patients with neck pain: a randomized controlled study. Arch Phys Med Rehabil. 1994; 75:895-899.

Roberts, et al. Proprioception in people with anterior cruciate ligament-deficient knees: comparison of symptomatic and asymptomatic patients. JOSPT. 1999; 29(10):587-594.

Roberts, et al. Mechanoreceptors in intervertebral discs Morphology, distribution, and neuropeptides. Spine. 1995; 20(24):2645-2651.

Schache, et al. The coordinated movement of the lumbo-pelvic-hip complex during running: a literature review. Gait and posture. 1999; 10:30-47.

Schmidt. Motor Control and Learning: A Behavioral Emphasis. 2nd ed. Champaign, Illinois: Human Kinetics Publishers Inc.; 1988.

Sharma, et al. Impaired proprioception and osteoarthritis. Current Opinion in Rheumatology. 1997; 9:253-258.

Shrout, et al. Intraclass correlations: uses in assessing rater reliability. Psychological Bulletin. 1986; 420-428.

Skinner, et al. Joint position sense in total knee arthoplasty. J. Orthop Research. 1984; 1:276-283.

Skinner, et al. Age-related decline in proprioception. Clin Orthop & Rel Research. 1984; 184:208-210.

Skinner, et al. Joint position sense in the normal and pathologic knee joint. Journal of Electromyography and Kinesioology. 1991; 1(3):180-190.

Skinner, et al. Effect of fatigue on joint position sense of the knee. J orthop Research. 1986; 4:112-118.

Taylor, et al. Proprioception in the neck. Exp Brain Res. 1988; 70:351-60.

Taylor, et al. Proprioceptive sensation in rotation of the trunk. Exp Brain Res. 1990; 81:413-416.

Tropp, et al. Stabilometry in functional instability of the ankle and its value in predicting injury. Medicine and science in sports and exercise. 1984; 16(1):64-66.

Tully. Lumbofemoral rhythm during hip flexion in young adults and children. Spine. 2002; 27(20):E432-E440.

Yahia, et al. Sensory innervation of human thoracolumbar fascia. Acta Orthop Scand. 1992; 63:195-7.

Yahia, et al. Neurohistology of lumbar spine ligaments. Acta Orthop Scand. 1988; 59:508-512.

Yamashita, et al. Mechanosensitive afferent units in the lumbar facet joint. The Journal of Bone and Joint Surgery. 1990; 72A(6):865-870.

Yamashita, et al. Mechanosensitive afferent units in the lumbar intervertebral disc and adjacent muscle. Spine. 1993; 18(15):2252-2256.

* cited by examiner

FIGURE 5. Mean Reposition Error trial (1-20) for 45 asymptomatic subjects.

FIGURE 6. Mean Reposition Error trial (1-20) for 15 symptomatic subjects.

SPINAL PROPRIOCEPTION METHODS AND RELATED SYSTEMS

This application claims priority benefit of U.S. Provisional Application No. 60/268,296 filed Feb. 13, 2001, the entirety of which is incorporated herein by reference.

FIELD OF THE INVENTION

The invention relates to a system, device and/or method for measuring spinal proprioception. The system, method and/or device are useful for screening proprioceptive loss and improvement after stabilization programs.

BACKGROUND OF THE INVENTION

Proprioception describes those sensations generated within the body, which contribute to an awareness of the relative orientation of body parts, both at rest and in motion. The proprioceptive system is dependent upon a complex interaction between afferent and efferent receptors. It relies on simultaneous activity in a number of types of mechanoreceptor afferent neurons. In the spine, mechanoreceptor afferents have been isolated in the paraspinal muscles, interspinous, supraspinous, flaval and anterior longitudinal ligaments, thoracolumbar fascia, capsule, lumbar intervertebral discs, and cervical, thoracic and lumbar facet joints. Mechanoreceptors provide information for reflex regulation of muscle tone and for awareness of position sense and movement sense. Recent studies reveal that muscle afferents are the primary mechanoreceptors for position and movement sense, while joint afferent receptors are most active at the limits of joint movement.

Joint movements cause tissues to become deformed, which creates excitation of mechanoreceptor neurons that innervate the area and initiation of action potentials. These action potentials are then conducted to either the spinal cord for a reflex regulation of muscle tone or to higher centers of the CNS for processing of the signal and an appropriate response. In the CNS, proprioceptive signals are interpreted against a background input from other sources including visual, auditory and vestibular systems. In addition to this afferent information, the CNS also has internally generated command signals regarding the timing, grading and destination of motor output.

Proprioception plays a vital role in normal joint function, and is classically measured through two types of tests designed to assess either position sense (awareness of the relative orientation of body parts in space) or movement sense (detection of movement and acceleration).

Recent work has identified proprioceptive deficits following joint injury. Glencross and Thornton found deficits in the ability to actively replicate passive ankle and foot positioning in the sagittal plane among patients with sprained ankles. Studies have also demonstrated a decrease in proprioceptive sensibility in the cervical spine with pain, and in the knee joint with osteoarthritis, ACL deficient knees and after surgical ACL replacements. When rehabilitation programs have addressed proprioceptive deficits, improvements in proprioception as well as function and pain level have been found.

In recent years there has been a growing interest in measuring proprioception in the spine. Recent studies have begun to investigate proprioception and the effect of injury in the spine; cervical spine, lumbar spine, thoracolumbar spine, and the trunk as a whole. Revel et al found a mean repositioning error in the cervical region of healthy subjects to be 3.31° (flexion) and 3.43° (extension). Maffey-Ward et al tested lumbar spine movement sense in healthy subjects returning to a neutral seated position from a flexed posture and measured a 2.6° repositioning error. Newcomer et al measured repositioning error of the lumbar spine in subjects, and found a 2.4° repositioning error for trunk flexion in healthy subjects. Brumagne et al measured lumbosacral position sense through active pelvic tilting, and determined a mean absolute repositioning accuracy of 2.17°.

Swinkels and Dolan measured repositioning error from thoracic, lumbar and sacral sites, determining a mean spinal repositioning error in the sagittal plane for movement half of full flexion to be 5.27+/−3.47°. Another study by Swinkels and Dolan also measured repositioning error from thoracic, lumbar and sacral sites, and determined the absolute repositioning error for movements to two-thirds of full flexion to be 4.75+/−2.63°. Taylor and McCloskey studied healthy subjects and found the mean of the absolute value of the errors in active alignment rotating their trunk by turning the head and shoulders to be 2.8° and for turning the hips under the shoulders to be 2.9°.

These studies established a range of absolute active repositioning errors, and therefore, any future studies developed to measure joint repositioning sense could be expected to have a repositioning error within the previously established limits. Although valuable findings were obtained from the studies, their devices/procedures are not suitable for the clinical setting. Many of the devices involve the attachment of substantial apparatus, providing additional cutaneous cues, which may facilitate proprioceptive acuity, as well as adding to the time intensiveness of the procedure. Parkhurst and Burnett created an apparatus for their study consisting of various table and seat configurations, but stated that the device would not be a useful diagnostic tool for clinical purposes secondary to its cumbersome nature and the time required for testing. Revel et al used a light beam mounted on a helmet and which projected onto a target grid to measure position sense in the cervical spine. Other previous studies have used the 3 Space Fastrak, 3 Space Tracker, and the Lumbar Motion Monitor, all requiring the attachment of sensors to the subject's skin and hence introducing additional cutaneous input. Maffey-Ward et al acknowledged that the sensors could provide feedback for the subject via cutaneous mechanoreceptors, contrary to the ideal environment for a proprioceptive test in which no other sensory cues are involved.

Various aspects relating to the prior art and/or skill therein can be found in the following references each of which is incorporated herein in its entirety:

Amonoo-Kuofi H S. The number and distribution of muscle spindles in human intrinsic postvertebral muscles. *J Anat* 1982;135:585–99.

Ashton-Miller J A, McGlashen K M, Schultz A B. Trunk positioning accuracy in children 7–18 years old. J Orthop Res 1992;10:217–25.

Barrack R L, Skinner H B, Buckley S L. Proprioception in the anterior cruciate deficient knee. *The American Journal of Sports Medicine* 1989;17(1):1–6.

Barrett D S, Cobb A G, Bentley G. Joint proprioception in normal, osteoarthritic and replaced knees. *J Bone Joint Surg [Br]* 1991;73:53–6.

Barrett D S. Proprioception and function after anterior cruciate reconstruction. *J. Bone Joint Surg Br* 1991;73: 833–837.

Brumagne S, Lysens R, Spaepen A. Lumbosacral position sense during pelvic tilting in men and women without low back pain: test development and reliability assessment. *JOSPT* 1999;29(6):346–351.

Corrigan J P, Cashman W F, Brady M P. Proprioception in the cruciate deficient knee. *J Bone Joint Surgery.* 1992; 74B:247–250.

Fairbanks J C et al. The oswestry low back pain disability questionnaire. *Physiotherapy.* 1980:6:271–273.

Fritz J M, Haddox A. Improving neuromuscular control following trunk and lumbar spine injury. *The professional journal for athletic trainers and therapists.* 1998;??: 19–28.

Freeman M, Dean M, Hanham I. The etiology and prevention of functional instability of the foot. J Bone Joint Surg. 47B:678–685, 1965.

Gandevia S C, Burke D. Does the nervous system depend on kinesthetic information to control natural limb movements? *Behavioral and Brain Sciences* 1992;15(4):614–63?.

Gandevia S C, Hall L A, McCloskey D I, Potter E K. Proprioceptive sensation at the terminal joint of the middle finger. *J Physiol* 1983;335:507–517.

Gandevia S C, McCloskey D I. Joint sense, muscle sense and their combination as position sense, measured at the distal interphalangeal joint of the middle finger. *J Phsiol* 1976;260:387–407.

Gill K P, Callaghan M J. The measurement of lumbar proprioception in individuals with and without low back pain. *Spine* 1998;23(3):371–377.

Glencross D, Thornton E. Position sense following joint injury. J Sports Med. 1981;21:23–27.

Goodwin G M, McCloskey D I, Matthews P B C. The persistence of appreciable kinesthesis after paralyzing joint afferents but preserving muscle afferents. *Brain Research* 1972;37:326–329. (get this)

Grigg P. Peripheral neural mechanisms in proprioception. *J Sport Rehabil* 1994;3:2–17.

Jakobs T, Miller J A A, Schultz A B. Trunk position sense in the frontal plane. Exp Neurol 1985;90:129–38.

Johannsen F, Remvig L, Kryger P, Beck P, Warming S, Lybeck K, Dreyer V, Larsen L H. Exercises for chronic low back pain: a clinical trial JOSPT 1995;22(2):52–59.

Kaplan F S, Nixon J E, Reitz M, Rindfleish L, Tucker J. Age-related changes in proprioception and sensation of joint position. *Acta Orthop Scand* 1985;56:72–74.

Lam S S K, Jull G, Treleaven J. Lumbar spine kinesthesia in patients with low back pain. *JOSPT* 1999;29(5):294–299.

Loudon J K, Ruhl M, Field Edelle. Ability to reproduce head position after whiplash injury. *Spine* 1997;22(8):865–868.

Maffey-Ward L, Jull G, Wellington L. Toward a clinical test of lumbar spine kinesthesia. *JOSPT* 1996;24(6):354–358.

Marks R, Quinney H A, Wessel J. Proprioceptive sensibility in women with normal and osteoarthritic knee joints Clinical Rheumatology 1993;12(2):170–175.

Martin J H, Jessell T M. Anatomy of the somatic sensory system. In: Kandel E R, Schwartz J H, Jessel T M, eds. Principles of Neural Science. Norwalk: Appleton & Lange, 1991;353–366.

Matthews P B C. Proprioceptors and their contribution to somatosensory mapping: complex messages require complex processing. *Can J Physiol Pharmacol* 1988;66:430–438.

McLain R F, Raiszadeh K. Mechanoreceptor endings of the cervical, thoracic, and lumbar spine. *Iowa Orthopedic Journal* 1995;15:147–155.

McLain R F. Mechanoreceptor endings in human cervical facet joints. *Spine* 1994;19:495–501.

Newcomer K, Laskowski E R, Yu B, Larson D R, An K. Repositioning error in low back pain. Comparing trunk repositioning error in subjects with chronic low back pain and control subjects. *Spine* 2000;25(2):245–250.

Parkhurst T M, Burnett C N. Injury and proprioception in the lower back. *JOSPT* 1994;19(5):282–295.

Revel M, Andre-Deshays C, Minguet M. Cervicocephalic kinesthetic sensibility in patients with cervical pain. *Arch Phys Med Rehabil* 1991;72:288–291.

Revel M, Minguet M, Gergoy P, Vaillant J, Manuel J L. Changes in cervicocephalic kinesthesia after a proprioceptive rehabilitation program in patients with neck pain: a randomized controlled study. Arch Phys Med Rehabil 1994;75:895–899.

Roberts D, Friden T, Zatterstrom R, Lindstrand A, Moritz U. Proprioception in people with anterior cruciate ligament-deficient knees: comparison of symptomatic and asymptomatic patients. *JOSPT* 1999;29(10):587–594.

Roberts S, Eisenstein S M, Menage J, Evans H, Ashton K. Mechanoreceptors in intervertebral discs Morphology, distribution, and neuropeptides *Spine* 1995;20(24):2645–2651.

Sharma L, Pai Y. Impaired proprioception and osteoarthritis. *Current Opinion in Rheumatology.* 1997;9:253–258.

Schmidt R A. *Motor Control and Learning: A Behavioral Emphasis.* $2^{nd}$ ed. Champaign, Ill.: Human Kinetics Publishers Inc; 1988:384–385.

Skinner H B, Barrack R L, Cook S D, Haddad R J. Joint position sense in total knee arthroplasty. Journal of Orthopaedic Research 1984;1:276–283.

Skinner H B, Barrack R L, Cook S D. Age-related decline in proprioception. *Clin Orthop & Rel Research* 1984;184: 208–210.

Skinner H B, Barrack R L. Joint position sense in the normal and pathologic knee joint. *Journal of Electromyography and Kinesiology.* 1(3):180–190, 1991.

Skinner H B, Wyatt M P, Hodgdon J A, Conrad D W, Barrack R L. Effect of fatigue on joint position sense of the knee. *J Orthop Research* 1986;4:112–118.

Swinkels A, Dolan P. Regional assessment of joint position sense in the spine. Spine 1998;23(5):590–597.

Swinkels A, Dolan P. Spinal position sense is independent of the magnitude of movement. *Spine* 2000;25(1):98–105.

Taimela S, Kankaanpaa M, Luoto S. The effect of lumbar fatigue on the ability to sense a change in lumbar position. *Spine* 1999;24(13):1322–1327.

Taylor J L, McCloskey D I. Proprioception in the neck. Exp Brain Res 1988;70:351–60.

Taylor, McCloskey D I. Proprioceptive sensation in rotation of the trunk. *Experimental Brain Research* 1990;81:413–416.

Tropp H, Ekstrand J, Gillquist J. Stabilometry in functional instability of the ankle and its value in predicting injury Medicine and science in sports and exercise 1984;16(1): 64–66.

Yahia L, Rhalmi S, Newman N, Isler M. Sensory innervation of human thoracolumbar fascia. *Acta Orthop Scand* 1992; 63:195–7.

Yahia L H, Newman N, Rivard C H. Neurohistology of lumbar spine ligaments. *Acta Orthop Scand* 1988;59: 508–512.

Yamashita T, Cavanaugh J M, El-Bohy A A, Getchell T V, King A I. Mechanosensitive afferent units in the lumbar facet joint. *The Journal of Bone and Joint Surgery* 1990; 72A(6):865–870.

Yamashita T, Minaki Y, Oota I, Yokogushi K, Ishii S. Mechanosensitive afferent units in the lumbar intervertebral disc and adjacent muscle. *Spine* 1993;18(15):2252–2256.

SUMMARY OF THE INVENTION

In light of the foregoing, it is an object of the present invention to provide a methodology and/or a system/device as can be used therewith to measure proprioception repositioning sense—quickly, easily and inexpensively within or outside any clinical setting, thereby overcoming various problems and deficiencies of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide a system/apparatus, including a proprioception repositioning device of the type more particularly described herein addressing both prior art concerns and meeting one or more objectives, such a device applicable to a broader system and/or method to assess spinal reposition sense and/or to assess or reassess treatment intervention in patients having proprioception deficiencies.

It can be an object of the present invention to provide a system/apparatus, in accordance herein, for use in conjunction with existing statistical treatments and/or computer programs or such analysis or related software developed hereafter to more fully utilize the present invention and realize the benefits available therefrom.

It can be another object of the present invention to provide a system, apparatus and/or general methodology for use in monitoring and/or evaluating proprioception training exercises/activities and/or retraining programs.

It can also be an object of the present invention to provide a method of improving repositioning sense, such a method preferably effectuated through use in conjunction with one or more of the apparatus and/or systems described herein. As a related objective, such methods may be used to decrease spinal pain, improve function and/or slow the onset of degenerative spinal processes.

It can also be an object of the present invention to provide a method and/or apparatus which clinically measures position and reposition sense within ranges otherwise available through methods and apparatus of the prior art.

It can also be an object of the present invention to provide an apparatus for assessing reposition sense of the thoracolumbar spine not requiring physical attachment to the test subject.

Other objects, features, benefits and advantages of the present invention will be apparent from the summary and the following descriptions of various preferred embodiments, and would be readily apparent to those skilled in the art having knowledge of various proprioception devices and techniques. Such objects, features, benefits and advantages will be apparent from the above as taken in conjunction with the accompanying examples, data, figures and all reasonable inferences to be drawn therefrom.

The present invention includes, in part, a system and/or apparatus, including a preferred spinal reposition sensing device, providing distinct advantages over existing technology. It will be understood by those skilled in the art that the system/apparatus of the present invention includes, consistent herewith, various embodiments as can be used in conjunction with the broader methods described herein, such embodiments not limited to any one apparatus design or structural configuration.

Accordingly, this invention can include a system for assessing, determining and/or measuring spinal position sense of a human test subject, such a system having 1) a vertical reference component; 2) a horizontal reference component; 3) a reference housing component substantially positioning one reference component perpendicular to the other; and 4) a substantially level seat component supporting the vertical reference component perpendicular therewith. In preferred embodiments, the reference components can include metric rules or yardsticks or other similar such linear measuring devices. The housing component is preferably arranged and configured for coordinated interaction of one reference component with another. Highly preferred embodiments engage each of the reference components in such a way as to promote the angular relationships described elsewhere herein. While one such preferred embodiment can have an enclosed configuration about the interacting reference components, various other structures and configurations which guide, position and coordinate such components are also contemplated as part of the present invention.

Regardless of any one system or apparatus used therewith, the present invention includes, in part, a clinical method of assessing spinal reposition sense. Such a method includes 1) providing a test subject engaged in thoracolumbar movement, the movement including a plurality of flexion positions within a range of motion through the sagittal plane; 2) selecting one flexion position having a vertical coordinate and a horizontal coordinate; 3) recording a subject reposition in the sagittal plane, the reposition sensed by the subject responsive to the selected position, and having vertical and horizontal coordinates; and 4) comparing the selected position with the recorded reposition. In preferred embodiments, both the selected positions and recorded repositions have horizontal and vertical coordinates measured at C7-T4 on the test subject. Positions are selected within the range of motion, but preferably include full flexion, one-third flexion and two-third flexion positions. After selection of one such flexion position, repositions can be recorded substantially without cutaneous and/or visual input.

Likewise, without regard to physical system and/or apparatus, the present invention can also include a method of using linear coordinates to determine angle of thoracolumbar flexion in the sagittal plane. Such a method includes 1) positioning a subject seated on a substantially level seating surface; 2) providing a vertical reference in conjunction with said seating surface and measuring a vertical linear coordinate at C7-T4 on the subject; 3) measuring a horizontal linear coordinate from the vertical reference at C7-T4, the horizontal coordinate at a right angle to the vertical reference; and 4) determining through a trigonometric relationship the angle of flexion of the thoracolumbar spine in the sagittal plane. As described more fully above, a test subject can be positioned throughout a range of motion within the sagittal plane, such positions including, but not limited to, one-third full flexion, two-thirds full flexion, and full flexion within the range of motion. After determining a selected angle of flexion, comparison can be made with vertical and horizontal linear coordinates and the corresponding angle of flexion of the subject, responsive to the selected angle, to assess reposition sense.

A preferred implementation of the present invention, for measuring spinal position sense in a human, includes having the subject sit in an upright starting/seating posture: sitting up straight with feet positioned shoulder width apart and fingertips touching the ipsilateral shoulders. Then, the subject bends forward keeping a neutral neck position to a full flexion range of motion position and to a position ⅔ of their full flexion range of motion. Horizontal and vertical measurements are taken through openings in the housing component. The horizontal measurement (X) is taken measuring the distance from the vertical rule to one spinous process from C7-T4, and the vertical measurement (Y) is taken at the point where the horizontal rule crosses the vertical rule. X and Y coordinates can be recorded for positions including but not limited to initial position, full range of motion position and an estimated ⅔ position. Calculation of the angle (theta) assumed on each trial is computed using the trigonometric relationship or equation, $\theta = \tan^{-1} X/Y$.

As described more fully below, the invention provides a method of diagnosing or evaluating deficits in spinal reposition sense in a human patient. This method can also be used to monitor the effectiveness of proprioception retraining programs by comparing the repositioning sense of a human subject before and after therapy.

DETAILED DESCRIPTION OF THE PREFERRED EMBODIMENT

Figure 1:
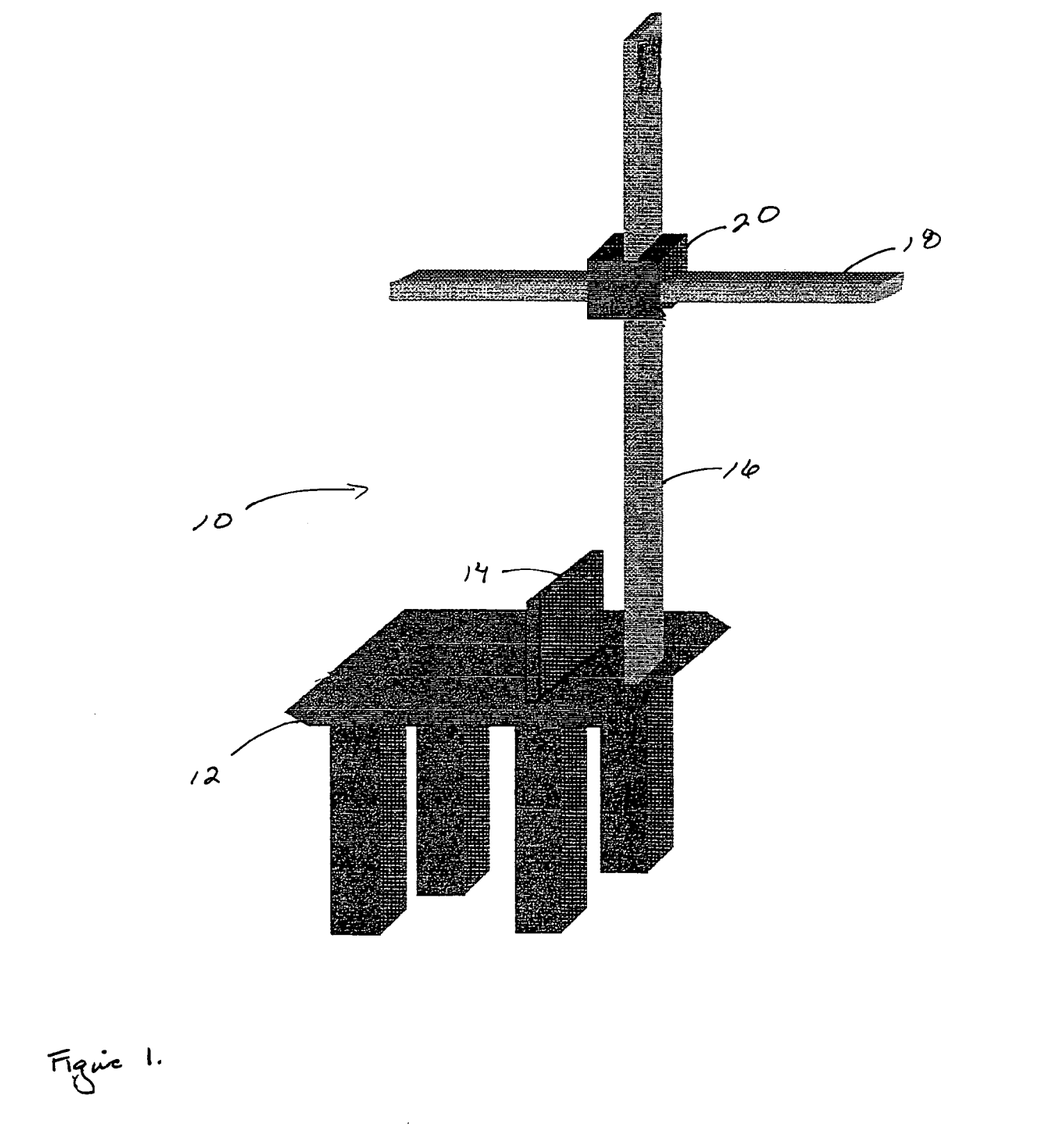
FIG. 1 shows schematically a preferred apparatus of this invention, in accordance with the broader aspects thereof, for measuring spinal reposition sense.
Figure 2:
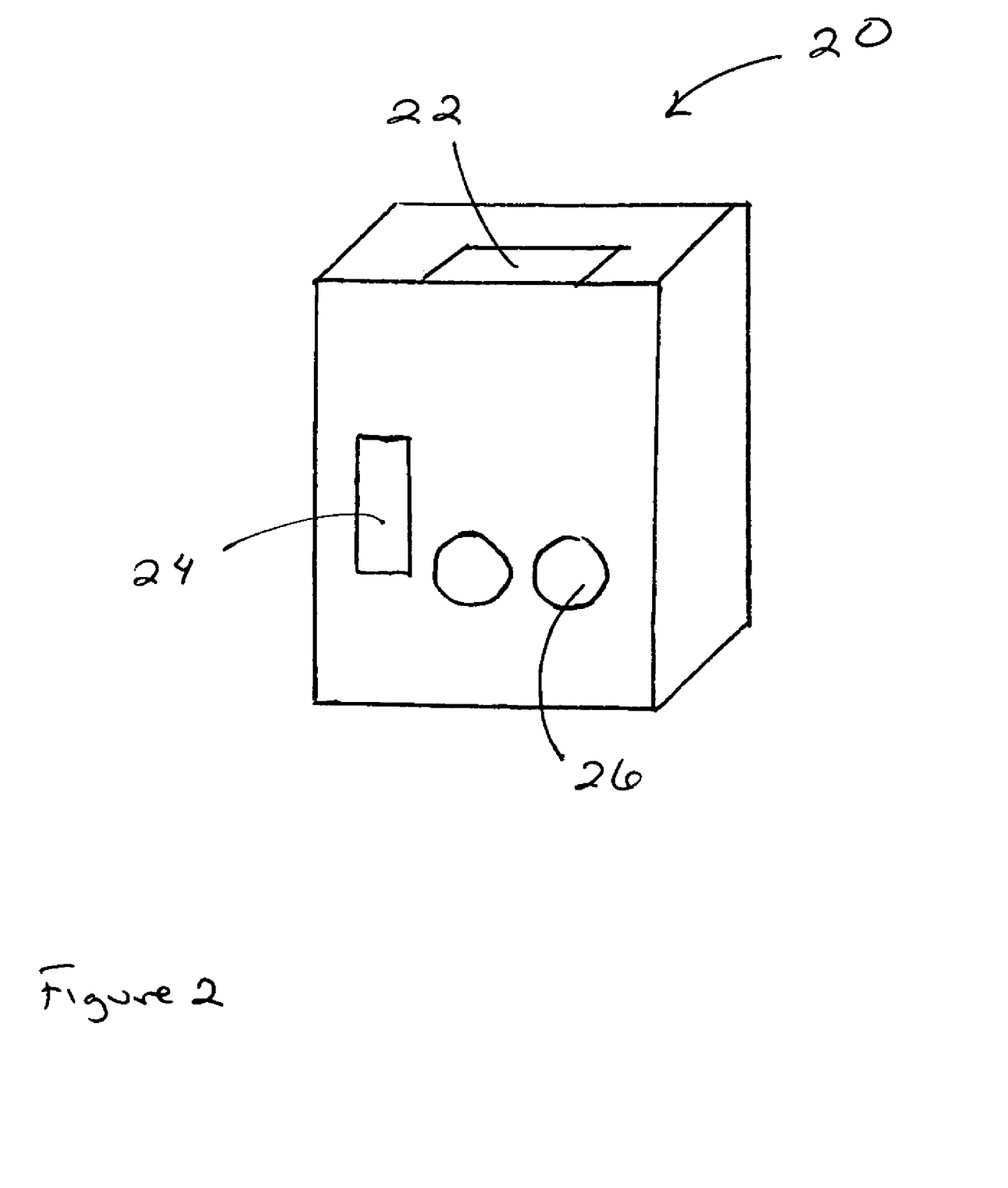
FIG. 2 shows schematically a preferred sliding/housing component of the apparatus of FIG. 1.

An apparatus/system for measuring spinal reposition sense is shown schematically in FIGS. 1 and 2. Apparatus 10 preferably includes stool 12 with a seating surface about 40 cm. from the floor, and preferably dimensioned about 30 cm wide×50 cm long. Vertical support member 14, preferably a flat piece of solid wood or other appropriate material (approximately 12 cm high×20–30 cm wide×2 cm thick) is perpendicular to the seating surface, approximately 14 cm from the 30 cm edge as a contact for the subject's lumbar spine region to serve as a location for the upright starting position. Behind lumbar contact support member 14, at the edge of the seating surface, is a measuring device consisting of two reference components, 16 and 18, and housing component 20. Reference component 16 is positioned vertically and perpendicular to the seating surface. Housing component 20 is positioned such that the vertical reference component 16 passes through top and bottom openings 22 thereof. (See, FIG. 2.) Housing component 20 can move up or down over/along component 16, allowing for measurement of a wide range of subject heights and ranges of spinal sagittal motion. The vertical measurement is taken through opening 26 within housing component 20 (FIG. 2). Horizontal reference component 18, optionally with an attached leveling device 28 (FIGS. 3–4), extends perpendicular to component 16 and passes through opening 24 in the housing component 20 (FIG. 2). The horizontal measurement is taken measuring the distance from vertical reference component 16 to a C7-T4 spinous process. The seating surface can be leveled with the floor, to ensure the apparatus provides the correct angular relationship and enables use of the aforementioned trigonometric equation in the analysis of reposition error.

EXAMPLES OF THE INVENTION

The following non-limiting examples and data illustrate various aspects and features relating to the systems/apparatus and/or methods of the present invention. In comparison with the prior art, such methods and systems/apparatus provide results and data which are surprising, unexpected and contrary to the prior art. While the utility of this invention is illustrated through the use of one or more methods and systems/apparatus which can be used therewith, it will be understood by those skilled in the art that comparable results are obtainable with various other apparatus structures, designs and configurations, as are commensurate with the scope of this invention.

Example 1

Measurement of Spinal Reposition Sense

A main objective of this example is to determine whether a device or system of this invention reliably measures reposition sense of the thoracolumbar spine in asymptomatic subjects within the realm of the literature. A secondary objective is to determine whether a difference in reposition sense of the thoracolumbar spine existed between asymptomatic subjects and subjects with back pain. The data of this example shows 1) that repositioning errors in healthy subjects compare with those of other studies of position sense in spinal joints, and 2) that symptomatic subjects will perform less accurately than asymptomatic subjects.

Subjects were recruited on a volunteer basis from Northwestern University, Department of Physical Therapy and Human Movement Sciences and included both students and faculty. Potential subjects were asked to complete the Oswestry Low Back Pain Questionnaire and a medical history. The subjects were then placed into two groups (asymptomatic and symptomatic) based on their Oswestry Questionnaire percentage score and information from the medical history form. A lower age limit of 18 years was set to target subjects with a fully developed proprioceptive system. An upper age limit of 40 years was set in an attempt to reduce the effect of age-related changes in position sense. Exclusionary criteria for both groups are presented in Table 1. 47 asymptomatic and 15 symptomatic subjects between the ages of 18 to 40 met the inclusion criteria and were tested. Five asymptomatic subjects were re-tested within 3–5 days after the initial testing for the purpose of test-retest reliability of the device.

Descriptive statistics for the subjects are presented in Table 2. Of the symptomatic subjects, three had received physical therapy including stabilization therapy for their back, one had undergone back surgery, one had a herniated disc one year prior, one had a history of juvenile rheumatoid arthritis, and one had a surgically repaired spondyloptosis. Eight of the fifteen symptomatic subjects were experiencing back pain the day of the testing. Two asymptomatic subjects (subjects 1 and 9) were excluded from the study because the first subject's data was verbalized which may have impacted performance, and the ninth subject was unable to focus on the task for the half-hour test duration.

PROCEDURE

Set-up Protocol

Subjects were instructed the day before testing not to perform any unaccustomed strenuous physical activity for 24 hours before testing and not to eat or drink two hours prior to testing to minimize cutaneous input from a distended abdomen. Testing occurred in a single session that lasted one half-hour for each subject. During testing, visual, auditory and cutaneous cues were controlled. Visual input was eliminated by blindfolding the subjects and auditory input was limited by keeping the room silent. In order to decrease the amount of cutaneous input, subjects were instructed to wear tight fitting shorts, females were asked to wear a halter top or sports bra and males were asked to remove their shirts for testing. In addition, subjects were asked to sit upright on their ischial tuberosities and place their fingertips on the ipsilateral shoulder to limit cutaneous cues from the arms. A couple subjects experienced wrist or shoulder discomfort in the selected arm position, therefore they were instructed to let their fingertips/arms rest up more in the air.

The subjects read and signed a consent form. All subjects were asked if they were experiencing any cervical, thoracic or lumbar pain that day to confirm that no changes had occurred since the questionnaires were completed. Subjects who reported cervical pain were screened by examiner #1 using active and passive range of motion (ROM) testing to determine if the subject experienced neck pain that would be irritated by the testing procedure. The subjects were then palpated in sitting by examiner #1 and an X was marked with a pen on the C7 spinous process. If measurements could not be taken from C7 secondary to spinal curvature and/or musculature, the mark was then adjusted between C7-T4 to ensure measurements were taken accurately and not extrapolated to the skin.

Figure 3:
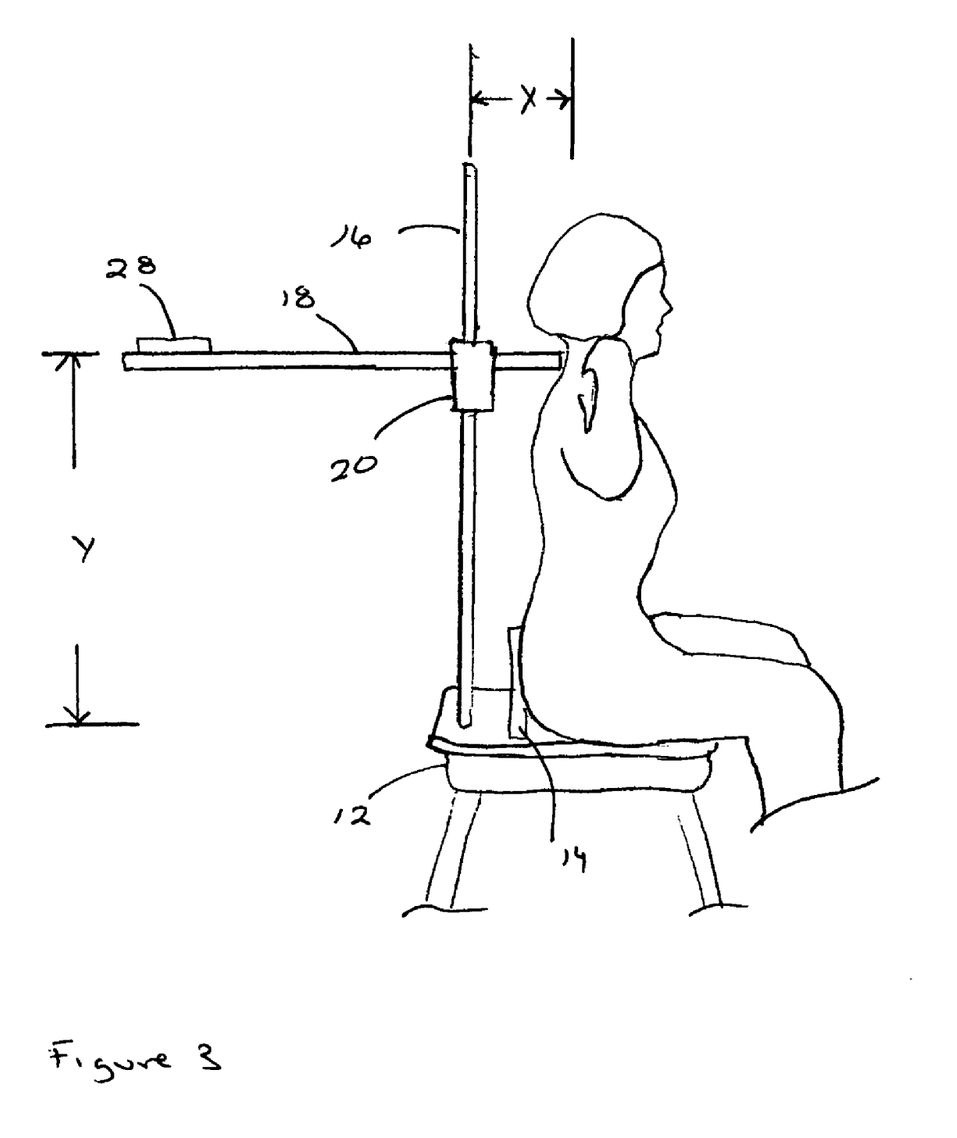
FIG. 3 illustrates schematically a subject in a starting posture (with X and Y coordinates), using the system, apparatus and/or method of this invention.

Subjects were then read standardized instructions by examiner #2. Subjects were asked to move toward the piece of wood bolted to the stool and stay sitting on their ischial tuberosities throughout testing. They were instructed their ischial tuberosities could roll, but not lift from the stool. Subjects were instructed the "upright starting posture" would include sitting up straight with feet positioned shoulder width apart and fingertips touching the ipsilateral shoulder (FIG. 3). Sitting allowed for a normal impact of gravity on the spinal structures. Subjects were told they would be asked to bend forward keeping a neutral neck position to a full flexion ROM position and to a position ⅔ of their full flexion ROM. Subjects were instructed to remember these positions in order to perform accurately throughout 20 subsequent reposition trials.

Data Collection

Figure 4:
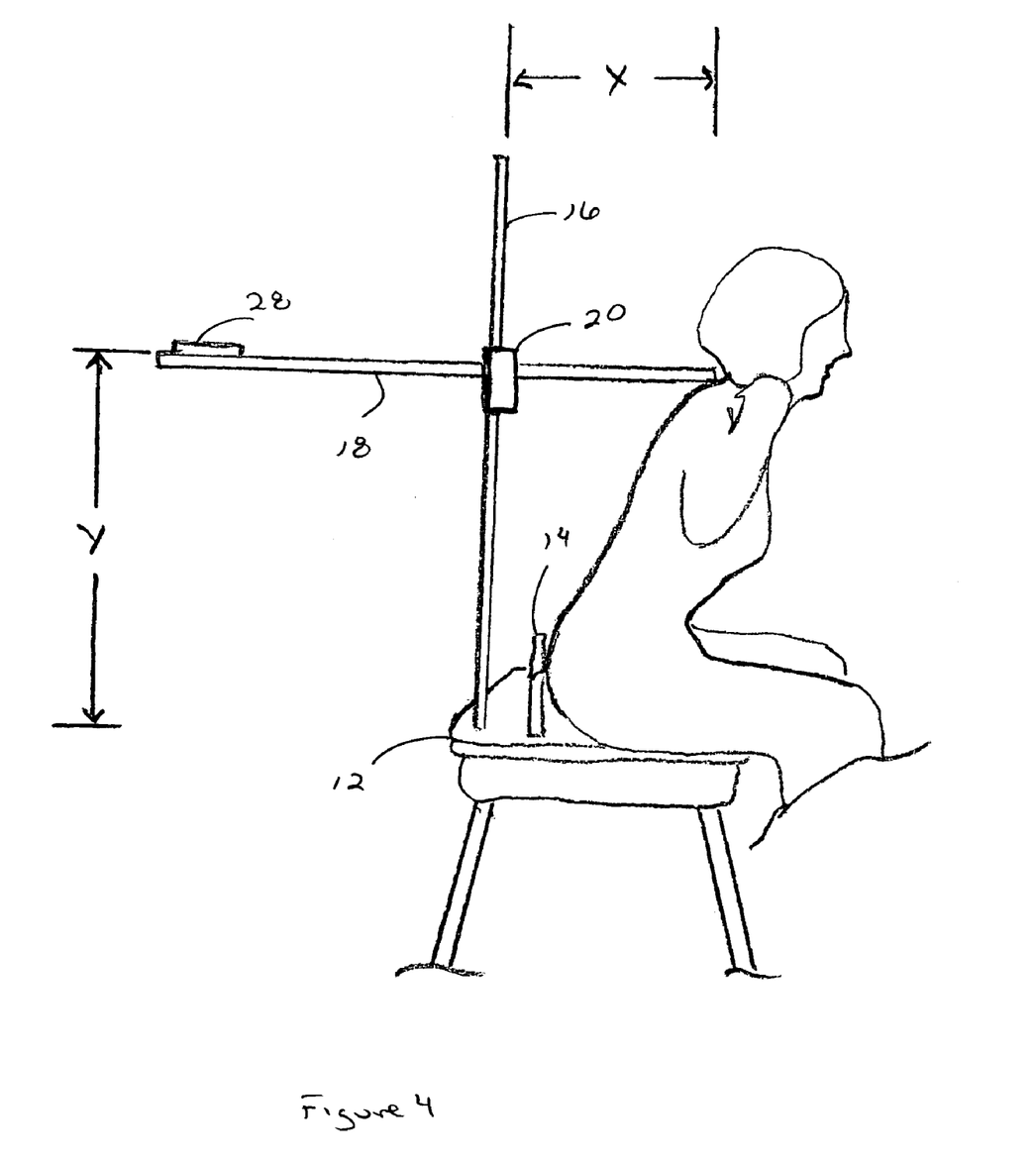
FIG. 4 illustrates schematically the subject of FIG. 3 in a flexion position (with X and Y coordinates) during use of the present invention.

Data was collected on 62 subjects total. The data for asymptomatic subjects 1 and 9 were excluded for the reasons stated previously. The measurement procedure was standardized and completed by examiner #2 to avoid inter-rater error. X and Y coordinates were recorded for the following positions: initial position (FIG. 1), full ROM position and an estimated ⅔ position (FIG. 4). The first ⅔ position was a practice trial and the following 20 trials were analyzed for reposition error in comparison with the practice trial. The subject was allowed to rest ten seconds between trials. Examiner #2 consistently measured using the bottom of the "X" marked on the spinous process. In the case of subjects who deviated in the frontal plane, a flat surface was used to line up the "X" with the horizontal yardstick. Examiner #2 wrote the data on a sheet of paper for all sets of data taken and examiner #1 recorded the data into an Office '97 Microsoft Excel spreadsheet designed for the study. The data was not verbalized to ensure the subject did not adjust their performance accordingly.

Example 2

Data Analysis

Figure 5:
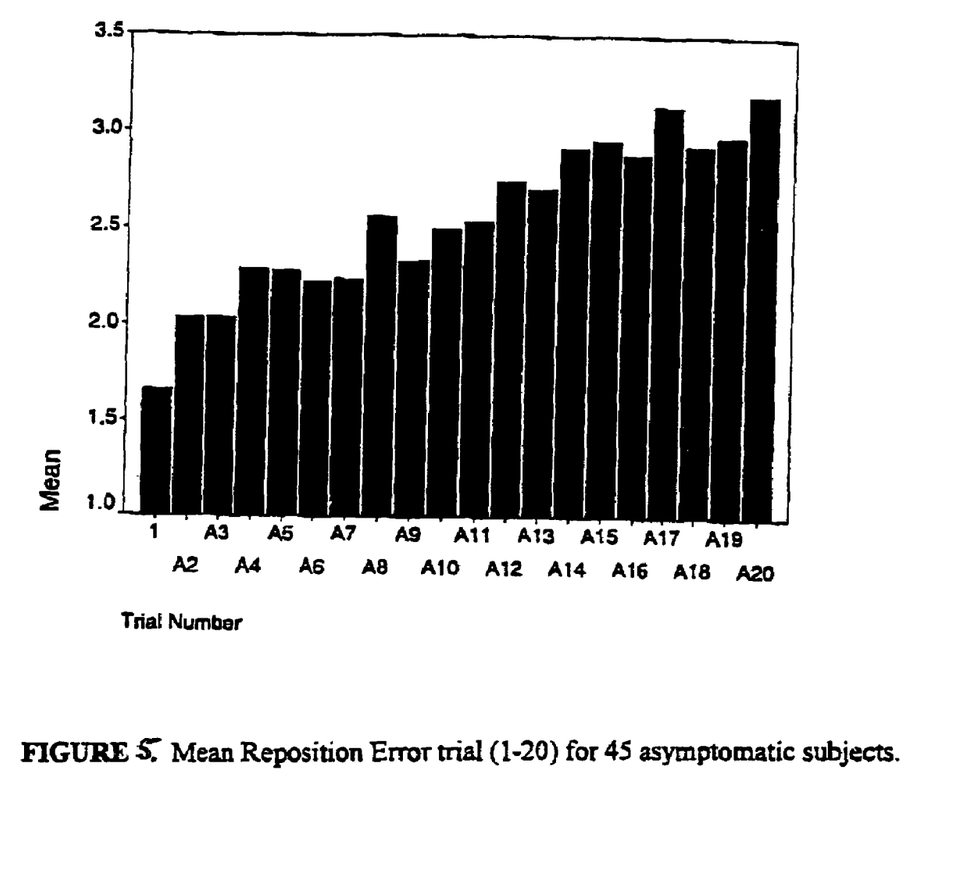
FIGS. 5 and 6 provide graphic data for asymptomatic and symptomatic subjects, respectively, demonstrating one or more utilitarian aspects of the present invention.
Figure 6:
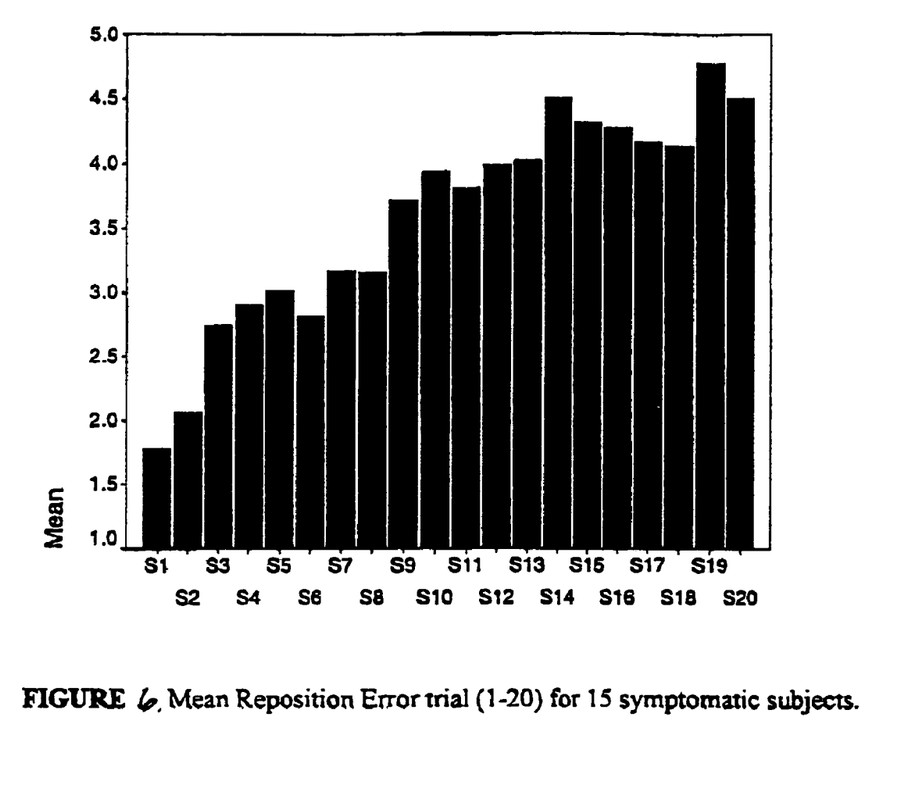

The data for 45 asymptomatic and 15 symptomatic subjects were analyzed. Calculation of the angle each subject assumed on all trials was computed using the trigonometric equation, $\theta=\tan^{-1} X/Y$. For the purpose of this illustrative example, reposition error was calculated for trials 1–20 as the difference between each trial ⅔ position and the initial ⅔ position performed during the practice trial. Absolute mean reposition error for each subject was calculated as the average of the sum of the reposition errors for trials 4–7. Trials 4–7 were chosen secondary to motor learning, fatigue, and oversampling issues determined from a graphical analysis (FIGS. 5 and 6). To quantitatively determine the unknown population mean, a 95% confidence interval (CI) was calculated from the mean absolute reposition error (ARE) and standard deviation (SD) for 20 trials.

Example 3

SPSS 8.0 was used to calculate a repeated measures two-way analysis of variance (ANOVA) using trials 4–7. Shrout and Fleiss calculations were used to calculate the Intraclass Correlation Coefficients (ICC 2,1) for the two populations to assess intraclass reliability. The independent t-test was used to compare the asymptomatic to symptomatic subjects to determine if there are differences between the two groups. The 45 asymptomatic subjects were randomized into three groups of 15 and compared to the group of 15 symptomatics. A paired t-test was performed for the test-retest group to determine day-to-day reliability of the device.

Example 4

A 95% confidence interval revealed that trials 4–7 fell within the limits of the CI for both populations. The mean ARE and SD for trials 4–7 and the range of ARE and a 95% CI for trials 1–20 are shown in Table 3. The ICC (2,1) for trials 4–7 was 0.97 for asymptomatic and 0.94 for symptomatic subjects. The paired t-test revealed the p-value for the test-retest subjects was non-significant. The independent t-test to compare the two populations revealed the p-value was non-significant.

Graphical analysis of the 20 trials shown in FIG. 5, displays this study over-sampled. In the asymptomatic population, motor learning occurred during trials 1–3, performance plateaued over trials 4–7, and fatigue began to hinder performance during trials 8–20. The same trends were seen in the symptomatic subjects as shown in FIG. 6, but there was a greater range of ARE as table 3 displays.

Under and overshooting the target ⅔ position was also documented. In the asymptomatic subjects, 24 overshot the target and 21 undershot the target, therefore approximately a 50/50 split. In the symptomatic subjects, 4 overshot the target and 11 undershot the target. All four of the subjects who overshot the target reported they had no back pain before or after testing. Of the eleven subjects who undershot the target, eight had pain before testing, two developed pain during testing, eight had an increase in their initial level of pain as a result of testing, and one remained pain free.

Example 5

Reliability

In this study, the mean ARE (2.32°) for asymptomatic subjects in the thoracolumbar spine while assuming a position ⅔ of full flexion was within the realm of the previous literature proprioception studies. In addition, the results of the ICC indicate good reliability of the apparatus/system of this invention, for the objective measurement of proprioception in a clinical setting.

The test-retest results did not indicate day-to-day reproducibility. Possible explanations for the results are that a small test population (N=5) was used for retesting. In addition, one of the five subjects displayed large differences in their reposition error between sessions and one subject was still experiencing significant muscle pain from the original testing session. Any future studies should use a larger test-retest population and subjects who present with minimal to no back pain between sessions in order to accurately assess the day-to-day reliability of the apparatus.

Example 6

Asymptomatic vs. Symptomatic Findings

The independent t-test did not reveal significant differences between the two test populations. One explanation is the exclusion criterion for the symptomatic population resulted in subjects that only represented minimal disability according to the Oswestry criteria. Newcomer et al reported that results may be influenced if the population tested does not have enough back dysfunction to affect afferent input. Glencross and Thornton report that the results of their study on ankle injuries concluded that error was found to be greatest in the most severely injured group and least for the mildly injured group. Therefore, individuals with minimal back pain may not have changes in their proprioceptive system. In addition, three of the symptomatic subjects had previously been involved in stabilization therapy, possibly influencing their performance. It is possible that secondary to proprioceptive training, these subjects may have been performing similar to the asymptomatic population despite their back pain history. Future studies should test a symptomatic population with more significant back problems and exclude subjects who have had stabilization therapy from the symptomatic group.

Previous studies investigating the possible relationship between back dysfunction and proprioception have had mixed findings. Gill and Callaghan tested individuals with and without chronic low back pain, and identified a significant spinal proprioceptive deficit among individuals with chronic low back pain in comparison to a group without back pain. Parkhurst and Burnett demonstrated altered lumbar proprioception among a group of fire fighters with low back pain. Revel et al investigated repositioning error in the cervical spine among healthy and symptomatic subjects, and found that symptomatic subjects performed significantly poorer than healthy subjects. Loudin et al also demonstrated deficits in the ability to reproduce target positions with the cervical spine among subjects who experienced whiplash in comparison to control subjects. Newcomer et al did not find significant differences in repositioning error between control subjects and those with chronic low back pain. Lam et al tested lumbar movement sense in subjects with low back pain, and determined that the symptomatic subjects performed more accurately than the asymptomatic subjects.

Example 7

Motor Learning

From FIGS. 5 and 6, it is seen that there was a motor learning component involved and one practice trial did not provide the subject enough practice to recall the position they were supposed to reproduce 20 times. Motor learning literature suggests that sessions of practice be structured to maximize learning, since under usual circumstances more practice leads to more learning. The data from this study revealed four practice trials was sufficient practice time to recall the initial ⅔ position and perform consistently.

Example 8

Influence of Fatigue and Pain on Performance

The graphs also revealed this study oversampled in using 20 trials. After eight trials, fatigue and performance become inversely related and reposition error increased. From a motor learning perspective, fatigue is known to become an issue when practice sessions are massed. The design of the testing session in this study may have influenced the onset of fatigue since the performance time was greater than the rest time. Taimela et al studied the effect of paraspinal muscle fatigue on the ability to sense a change in lumbar position and reported that lumbar fatigue impairs proprioception. Skinner et al studied position sense of the knee joint before and after fatigue and found a decrease in position sense with fatigue. Although it was not an objective of this study, previous literature and the data from this study support the premise that fatigue impairs proprioception. Performance is decreased presumably through the loss of efficiency of the muscle receptors once fatigued, since muscle receptors are thought to be the primary proprioceptive receptor. The effects of fatigue may be limited in future studies by reducing the number of test trials or by designing a distributed testing session in which the performance and rest time are more equivalent.

Example 9

Studies have suggested pain afferents may provide additional afferent information and affect position sense performance. As a result of the large range of motion, symptomatic subjects experienced increased pain during this study. Symptomatic subjects may have used the intensity of pain that they experienced as a guide for position sense. This may have increased the reposition acuity of symptomatic subjects, secondary to using pain as an extra afferent input. This also could have contributed to decreased reposition acuity secondary to the subject undershooting the target position after experiencing pain. In future studies, it would be beneficial to use a smaller range of motion and test subjects who are not experiencing pain at the time of testing, in order to eliminate the impact pain afferents have on proprioceptive performance.

Example 10

This study tested subject's proprioception in the sagittal plane because the apparatus does not measure movement in the frontal and transverse planes. Although this study attempted to maximally decrease the amount of tactile cues that could facilitate proprioceptive performance, it is not possible to completely eliminate all tactile cues. Subjects may have received tactile cues through contact of the ischial tuberosities with the stool, and their abdomen with their shorts. The Oswestry Low Back Pain Questionnaire was one of the tools used to categorize symptomatic and asymptomatic subjects, but was not the most appropriate pain questionnaire since this study measured position sense in the thoracolumbar spine. Other embodiments can include a general back pain questionnaire to screen subjects. Changing the C7-T4 skin mark, depending on the individual, introduced variability. Other embodiments can use only T4 as the skin mark to reduce variability. It should be mentioned, of course, that this study was not blinded.

Example 11

Clinical Relevance

Many clinicians are currently prescribing proprioceptive training programs for patients with back problems. The justification of carrying out proprioceptive exercises for the low back has largely been based on clinical knowledge and proprioception literature from the peripheral joints. Revel et al measured a significant improvement in cervical repositioning accuracy among symptomatic subjects following a proprioceptive rehabilitation program with a device created for their study. O'Sullivan et al reported a significant reduction in pain intensity and disability levels following a 10-week specific training program for the deep abdominal muscles with co-activation of the lumbar multifidus. Studies by Hagins et al and Hides et al investigated lumbar muscle recovery in subjects with acute low back pain and discovered that a 4-week exercise program designed to re-educate the multifidus muscle in its stabilizing role expedited muscle recovery and one's ability to perform difficult lumbar stabilization exercises. Despite these findings, research supports there is a lack of correlation between muscle wasting and symptoms, therefore an objective measurement is needed to assess paraspinal muscle function and proprioceptive capacity in patients with LBP. Direct objective measurement of muscle/proprioceptive performance might aid in the selection of an appropriate treatment choice. Initial screening of patients with spinal problems or LBP for proprioceptive loss, and subsequent testing upon completion of a proprioceptive training program is currently needed to justify the efficacy of stabilization programs. The examples of this invention have demonstrated that the present apparatus/system can be used for spinal proprioception measurements in the sagittal plane.

TABLE 1

Exclusionary criteria for asymptomatic (A) and symptomatic (S) subjects.

| Exclusionary Criterion (by self-report) | A | S |
|---|---|---|
| Oswestry back pain scores of greater than or equal to 5% | X | |
| Oswestry back pain scores of <5% or >60% | | X |
| Back pain for less than one month | | X |
| Balance, coordination, or stabilization therapy within the last six months | X | |
| Excessive use of pain medication, drugs, or alcohol | X | |
| Ligamentous injury to the hips, pelvis, or spine | X | |
| Spinal surgery | X | |
| Balance disorders secondary to: active or recent ear infections, vestibular disorders, trauma to the vestibular canals, or orthostatic hypotension | X | |
| Neurologic disorders including: multiple sclerosis (MS), cerebral vascular accident (CVA), spinal cord injury, neuropathies, and myopathies | X | X |

TABLE 1-continued

Exclusionary criteria for asymptomatic (A) and symptomatic (S) subjects.

| Exclusionary Criterion (by self-report) | A | S |
|---|---|---|
| Diseases of the spine including: osteoporosis, instability, fractures, rheumatoid arthritis (RA), degenerative disc disease (DDD), and spondylolisthesis. | X | |
| Unrepaired spondylolisthesis | | X |

TABLE 2

Descriptive statistics for subject characteristics and history.

| Characteristic | | Asymptomatic | Symptomatic |
|---|---|---|---|
| Age: (years) | Mean | 25.6 | 25.3 |
| | SD | 4.2 | 4.2 |
| | Range | 22–40 | 23–40 |
| Sex: | Ratio male:female | 8:37 | 4:11 |
| Height: (inches) | Mean (female, male) | 65.8, 70.8 | 65.5, 70.6 |
| | SD (female, male) | 2.8, 3.4 | 2.5, 4.8 |
| | Range (female, male) | 60–74, 64–76 | 60–69, 64–76 |
| Weight: (pounds) | Mean (female, male) | 129.6, 189.8 | 127.5, 173.5 |
| | SD (female, male) | 18.9, 30.7 | 10.3, 35.2 |
| | Range (female, male) | 95–175, 150–245 | 108–150, 140–220 |
| Handedness: | Ratio left:right | 4:41 | 0:15 |
| Oswestry LBP Questionnaire: | | | |
| | Mean % score | 1.0% | 11.0% |
| | Range | 0–4.4% | 2.0–18.0% |

TABLE 3

Group mean Absolute Reposition Error (ARE) and Standard Deviation (SD) calculated for trials 4–7* (in degrees). Range and 95% confidence interval (CI) based on 20 trials.

| | Mean ARE | SD | Range | 95% CI |
|---|---|---|---|---|
| Asymptomatics | 2.32 | 0.21 | 1.66–3.20 | 1.74–3.37 |
| Symptomatics | 2.78 | 0.63 | 1.90–4.78 | 1.89–5.11 |

*A window of trials 4–7 was chosen since the mean ARE for both populations fell within a 95% CI using trials 1–20.

Example 12

Spine degeneration is part of the normal process of aging. Decreases in the ability to sense one's position in space (proprioception) have been found to occur both with degenerative disease and with aging. Decreases in proprioception have been hypothesized to increase the degenerative process. If proprioception could be improved, the degenerative process may be slowed. Clinically, this has relevance, because pain and loss of function coincide with joint degeneration. By improving proprioception, pain could be decreased and function improved. Twenty-five subjects are tested using an apparatus/system, in accordance with this invention, that measures spine reposition sense. Radiographic measurements of each subject's lumbar spine degeneration are secured from the patient's medical record. Each subject performs 7 repetitions of two-thirds of their pain free trunk flexion range of motion.

Protocol Summary

A total of 25 subjects between the ages of 20–65 years old are recruited for this study. Subjects may be male or female. Subjects under 20 are excluded because significantly less degenerative spinal changes will be present in this group and subjects between 20–65 are likely to show a wide variety of age related degenerative spinal changes. Subjects are recruited from two to three physician practices. Presence of degenerative spinal changes are confirmed by review of a recent spinal radiograph (i.e. within one year) from the patient's existing medical record. Based on the radiology report, subjects are classified as showing 1 to 4 degrees of degenerative changes. Additional criteria for exclusion of subjects includes an inability to perform trunk flexion movements in a sitting position, an Oswestry disability score less than 30% or greater than 80%; balance, coordination or stabilization therapy within the past 6 months; excessive use of pain medication, drugs, or alcohol; cervical pain with active or passive range of motion (ROM) tests; ligamentous injury to the hips, pelvis or spine; any history of spinal surgery; balance disorders secondary to active or recent ear infections, vestibular disorders, trauma to the vestibular canals, or orthostatic hypotension; neurologic conditions including: multiple sclerosis, cerebral vascular accident, spinal cord injury, neuropathies, myopathies; and specific diseases of the spine including: osteoporosis, fractures, rheumatoid arthritis, and unrepaired spondylolisthesis.

Each subject signs an informed consent prior to any testing. In the pretest screening, subjects complete a medical information form, a Visual Analog Pain Scale, and the Oswestry disability questionnaire. The information form screens for any medical history that would render the subject ineligible for further testing, and includes information on the frequency of low back pain episodes and associated traumas. The Visual Analog Pain Scale asks them to rate their current level of pain to exclude subjects with current episodes of back pain. The Oswestry disability questionnaire gives a percentage score of each subject's level of functional disability and must be greater than 30% but less than 80% to be eligible for participation.

Subjects are instructed not to perform any unaccustomed strenuous physical activity for 24 hours before testing and to not eat or drink two hours prior to testing. In order to decrease cutaneous input, male subjects are asked to perform the testing protocol without a shirt on. Female subjects will be asked to wear a halter-top issued to them during testing. Each subject's T4 spinous process is marked with a skin pencil.

Measurement procedures are standardized for the screening process. One evaluator marks the T4 spinous process, performs active and passive ROM tests on subjects, and records proprioception measurements. A second evaluator instructs subjects with the testing procedure and reads measurements from the device.

The repositioning accuracy of the spine is measured using a device in accordance with this invention, previously tested and found to provide reliable measurements. The device consists of two metric yardsticks and a sliding mechanism, as more fully described above. One yardstick is positioned vertically and the second yardstick extends perpendicularly to the vertical yardstick. The yardstick that extends horizontally has a level attached, and the vertical yardstick will be leveled to the underlying surface, a wooden stool that the entire device is bolted to. The stool will be leveled to the floor. A flat piece of wood bolted to the bottom edge of the vertical yardstick extends anteriorly to serve as contact for the subject's lumbar region. The horizontal yardstick comes to a point at the end and will slide horizontally to make contact with the T4 spinous process. The vertical yardstick can slide up or down, allowing for measurement of a wide range of subject heights and ranges of spinal sagittal motion.

Subjects are instructed to sit on their ischial tuberosities with their back resting against the flat contact surface on the wooden bench. The subject's feet are positioned flat on the floor and will remain in that position throughout the test. The subject is blindfolded to eliminate visual input. The subject is asked to perform repositioning within their pain free spinal flexion ROM. One full, painfree flexion ROM is assessed. The subject is then asked to assume a position that is one-half of that painfree trunk flexion ROM, and to feel and recognize that position. Seven trials performed by each subject to reposition to that two-thirds pain free flexion position are measured with the described device.

Calculation of the angle the subject assumes in each trial will be computed in conjunction with the aforementioned trigonometric relationship, using the vertical and horizontal measurements. The vertical measurement is read through an opening within the sliding mechanism, and the horizontal measurement is the distance from the vertical yardstick to the T4 spinous process. Multiple regression analyses are performed to examine the correlation between age, degree of degenerative changes, and frequency of previous low back pain episodes with repositioning ability in the spine.

While the principles of this invention have been described in connection with specific embodiments, it should be understood clearly that these descriptions are added only by way of example and are not intended to limit, in any way, the scope of this invention. Other advantages and features will become apparent from the claims filed hereafter, with the scope of such claims as determined by the reasonable equivalents and as understood by those skilled in the art.

What is claimed is:

1. A clinical method of assessing spiral reposition sense, said method comprising:
    providing a test subject engaged in thoracolumbar movement, said movement comprising a plurality of flexion positions within a range of motion through the sagittal plane;
    selecting one said flexion position, said position having a vertical coordinate and a horizontal coordinate;
    recording a subject reposition in said sagittal plane, said reposition sensed by said subject responsive to said selected position, said reposition having a vertical coordinate and a horizontal coordinate; and
    comparing said reposition with said selected position.

2. The method of claim 1 wherein said selected position and said recorded reposition have a horizontal coordinate measured at C7-T4.

3. The method of claim 2 wherein said horizontal coordinate is measured at the T4 spinal process.

4. The method of claim 1 wherein said subject is asymptomatic.

5. The method of claim 1 wherein said plurality of flexion positions are selected from the group consisting of full flexion range of motion, one-third flexion range of motion and two-thirds flexion range of motion.

6. The method of claim 1 wherein said recorded reposition comprises a recordation average.

7. The method of claim 1, wherein said subject reposition is substantially without cutaneous input.

8. The method of claim 1 wherein said subject reposition is substantially without visual input.

9. A method of using linear coordinates to determine angle of thoracolumbar flexion in the sagittal plane, said method comprising:
    positioning a subject seated on a substantially level seating surface;

providing a vertical reference and measuring a vertical linear coordinate at C7-T4 on said subject;

measuring a horizontal linear coordinate from said vertical reference at C7-T4 on said subject, said horizontal coordinate at a right angle to said vertical reference; and trigonometrically determining an angle of flexion of the thoracolumbar spine in the sagittal plane with said measured linear coordinates.

10. The method of claim 9 wherein said subject is seated at a distance apart from said vertical reference.

11. The method of claim 9 wherein said subject is positioned throughout a range of motion within the sagittal plane.

12. The method of claim 11 wherein said subject is positioned at least one of one-third full flexion and two-thirds full flexion range of motion.

13. The method of claim 9 wherein said determination assesses thoracolumbar reposition sense.

14. A method of using a system for determining thoracolumbar position in the sagittal plane to clinically assess spinal reposition sense, said method comprising:

providing a thoracolumbar measurement system having a vertical reference component, a horizontal reference component and a reference housing component, said vertical and horizontal reference components positioned substantially perpendicular one to another within said housing component, and a substantially level seat component supporting said vertical reference component substantially perpendicular therewith;

engaging a test subject seated on said system in thoracolumbar movement, said movement comprising a plurality of flexion positions within a range of motion through the sagittal plane;

selecting one said flexion position, said position having a vertical coordinate and a horizontal coordinate;

recording a subject reposition in said sagittal plane, said reposition sensed by said subject responsive to said selected position, said reposition having a vertical coordinate and a horizontal coordinate; and comparing said reposition with said selected position.

15. The method of claim 14 wherein said selected position and said recorded reposition have vertical and horizontal coordinates measured at C7-T4 on said subject.

16. The method of claim 14 wherein said subject is positioned throughout a range of motion within the sagittal plane.

17. The method of claim 14 wherein said subject reposition is substantially without cutaneous input.

18. The method of claim 14 wherein said subject reposition is substantially without visual input.

* * * * *

UNITED STATES PATENT AND TRADEMARK OFFICE
CERTIFICATE OF CORRECTION

PATENT NO. : 6,969,360 B1
APPLICATION NO. : 10/075120
DATED : November 29, 2005
INVENTOR(S) : Clive Pai et al.

It is certified that error appears in the above-identified patent and that said Letters Patent is hereby corrected as shown below:

Col. 2, Line 12: "movment" should be --movements--

Col. 3, Line 2: "346-351" should be --345-351--

Col. 12, Line 17: "become" should be --became--

Col. 16, Line 32: "spiral" should be --spinal--

Signed and Sealed this

Twenty-second Day of August, 2006

JON W. DUDAS
*Director of the United States Patent and Trademark Office*